United States Patent
Zadrozny et al.

(10) Patent No.: US 11,348,021 B2
(45) Date of Patent: May 31, 2022

(54) ASSISTING PROSPECT EVALUATION IN OIL AND GAS EXPLORATION

(71) Applicant: International Business Machines Corporation, Armonk, NY (US)

(72) Inventors: Bianca Zadrozny, Rio de Janeiro (BR); Renato Fontoura de Gusmao Cerqueira, Rau Ipanema (BR); Bruno da Costa Flach, Rio de Janeiro (BR); Ulisses T. Mello, Sao Paulo (BR)

(73) Assignee: International Business Machines Corporation, Armonk, NY (US)

( * ) Notice: Subject to any disclaimer, the term of this patent is extended or adjusted under 35 U.S.C. 154(b) by 716 days.

(21) Appl. No.: 16/367,529

(22) Filed: Mar. 28, 2019

(65) Prior Publication Data
US 2020/0311584 A1   Oct. 1, 2020

(51) Int. Cl.
| | |
|---|---|
| *G06N 5/04* | (2006.01) |
| *G06F 16/9538* | (2019.01) |
| *G01N 33/24* | (2006.01) |
| *G01V 8/02* | (2006.01) |
| *E21B 49/00* | (2006.01) |
| *E21B 47/00* | (2012.01) |

(52) U.S. Cl.
CPC .............. *G06N 5/048* (2013.01); *E21B 47/00* (2013.01); *G01N 33/241* (2013.01); *G01V 8/02* (2013.01); *G06F 16/9538* (2019.01); *E21B 49/00* (2013.01)

(58) Field of Classification Search
CPC .......... E21B 41/00; E21B 47/00; E21B 49/00; G01N 33/241; G01V 8/02; G06F 16/9538; G06N 20/00; G06N 5/048
See application file for complete search history.

(56) References Cited

U.S. PATENT DOCUMENTS

| | | | |
|---|---|---|---|
| 7,467,044 B2 | 12/2008 | Tran et al. | |
| 8,577,613 B2 | 11/2013 | Bryant et al. | |
| 8,749,549 B2 | 6/2014 | Hantschel et al. | |
| 9,262,721 B2 | 2/2016 | Hegazy et al. | |
| 2007/0038378 A1* | 2/2007 | Gelfand | G01S 17/89 702/13 |

(Continued)

OTHER PUBLICATIONS

Bickel, Eric J. et al.; "Optimal Sequential Exploration: A Binary Learning Model"; informs; Decision Analysis; vol. 3 No. 1; Mar. 2006; pp. 16-31; Copyright 2006 INFORMS.

(Continued)

*Primary Examiner* — Mark R Gaworecki
(74) *Attorney, Agent, or Firm* — Stephanie L. Carusillo

(57) ABSTRACT

A system, method and program product for evaluating a prospect. The method includes: receiving prospect information regarding a prospect for natural resource exploration; extracting a set of characteristics based on the prospect information; identifying a set of similar prospects and a set of prospect exploration results, based on the set of characteristics; receiving a success estimate for the prospect; validating the success estimate based on the set of characteristics, the set of similar prospects, and the set of prospect exploration results to determine inconsistencies in the success estimate; and approving the success estimate or receiving an updated success estimate, based on the inconsistencies in the success estimate.

20 Claims, 3 Drawing Sheets

(56) References Cited

U.S. PATENT DOCUMENTS

| | | | |
|---|---|---|---|
| 2008/0172179 A1* | 7/2008 | Tran | G06Q 10/06 702/6 |
| 2011/0118983 A1 | 5/2011 | Rowan | |
| 2014/0136466 A1 | 5/2014 | Hegazy et al. | |
| 2015/0254567 A1* | 9/2015 | Imhof | G01V 99/005 703/10 |
| 2018/0113962 A1 | 4/2018 | Babin et al. | |

OTHER PUBLICATIONS

Bickel, Eric J. et al.; "Modeling Dependence Among Geologic Risks in Sequential Exploration Decisions"; SPE Reservoir Evaluation & Engineering; Apr. 2008; pp. 352-361; Copyright 2008 Society of Petroleum Engineers.

Dyer, James S. et al.; "A Decision Support System for Prioritizing Oil and Gas Exploration Activities"; Operations Research; vol. 38; No. 396; May-Jun. 1990; Publisher: Institute for Operations Research and the Management Sciences (INFORMS); pp. 386-; Copyright 1990 INFORMS.

Mello, Ulisses; "AI and the Future of Oil"; IBM Research—Brazil; Jul. 5, 2018; pp. 2.

Perez-Valiente, M.L et al.; "Reservoir Analogues in the Presence of Uncertainty"; Society of Petroleum Engineers SPE Intelligent Energy Conference & Exhibition; Apr. 1-3; Publication 2014; Copyright SPE; pp. 2.

Malvic T.; "Stochastical approach in deterministic calculation of geological risk-theory and example"; Presentation from Scientific and Expert Gatherings; NAFTA 60; 12; 2009; pp. 651-657.

Ruffo, Paolo et al.; "Hydrocarbon exploration risk evaluation through uncertainty and sensitivity analyses techniques"; Reliability Engineering & System Safety; vol. 91; Issues 10-11; Oct.-Nov. 2006; pp. 1155-1162.

Hodgin, John Edgar, et al.; "The Selection, Application, and Misapplication of Reservoir Analogs for the Estimation of Petroleum Reserves"; SPE Annual Technical Conference and Exhibition; Sep. 24-27; San Antonio, Texas; Publication Date 2006; pp. 2; <https://doi.org/10.2118/102505-MS>.

* cited by examiner

ASSISTING PROSPECT EVALUATION IN OIL AND GAS EXPLORATION

TECHNICAL FIELD

The subject matter of this disclosure relates to fossil fuel exploration, and more particularly to a system and method for assisting the evaluation of prospects in oil and gas exploration.

BACKGROUND

As global energy consumption increases and much of the globe still relies on fossil fuels to supply its energy needs, the oil and gas industry continues to face the challenge of finding new resources. One of the most important and challenging technical activities in locating new resources is the evaluation and ranking of prospects for exploration.

In the oil and gas industry, a prospect is a potential trap which geologists believe may contain hydrocarbons. Justification for drilling a prospect is generally made by assembling evidence for an active petroleum system, or reasonable probability of encountering reservoir-quality rock, a trap of sufficient size, adequate sealing rock, and appropriate conditions for generation and migration of hydrocarbons to fill the trap. To this extent, determination of the exploration risk of a prospect necessarily involves a significant amount of geological, structural, and seismic investigation, analysis, and corresponding data. As new data arrives, such as data regarding new seismic acquisitions or results of drilling in exploration wells in similar (or analogous) prospects around the world, the risk evaluation of a prospect is impacted.

SUMMARY

A first aspect discloses a method for evaluating a prospect, the method including: receiving prospect information regarding a prospect for natural resource exploration; extracting a set of characteristics based on the prospect information; identifying a set of similar prospects and a set of prospect exploration results, based on the set of characteristics; receiving a success estimate for the prospect; validating the success estimate based on the set of characteristics, the set of similar prospects, and the set of prospect exploration results to determine inconsistencies in the success estimate; and approving the success estimate or receiving an updated success estimate, based on the inconsistencies in the success estimate.

A second aspect discloses a computer program product stored on a computer readable storage medium, which when executed by a computing system, evaluates a prospect, the program product including program code for: receiving prospect information regarding a prospect for natural resource exploration; extracting a set of characteristics based on the prospect information; identifying a set of similar prospects and a set of prospect exploration results, based on the set of characteristics; receiving a success estimate for the prospect; validating the success estimate based on the set of characteristics, the set of similar prospects, and the set of prospect exploration results to determine inconsistencies in the success estimate; and approving the success estimate or receiving an updated success estimate, based on the inconsistencies in the success estimate.

A third aspect discloses a system for evaluating a prospect, the system including a prospect evaluation assistant configured for: receiving prospect information regarding a prospect for natural resource exploration; extracting a set of characteristics based on the prospect information; identifying a set of similar prospects and a set of prospect exploration results based on the set of characteristics; receiving a success estimate for the prospect; validating the success estimate based on the set of characteristics, the set of similar prospects, and the set of prospect exploration results to determine inconsistencies in the success estimate; and approving the success estimate or receiving an updated success estimate based on the inconsistencies in the success estimate.

BRIEF DESCRIPTION OF THE DRAWINGS

These and other features of this invention will be more readily understood from the following detailed description of the various aspects of the invention taken in conjunction with the accompanying drawings.

Figure 1:
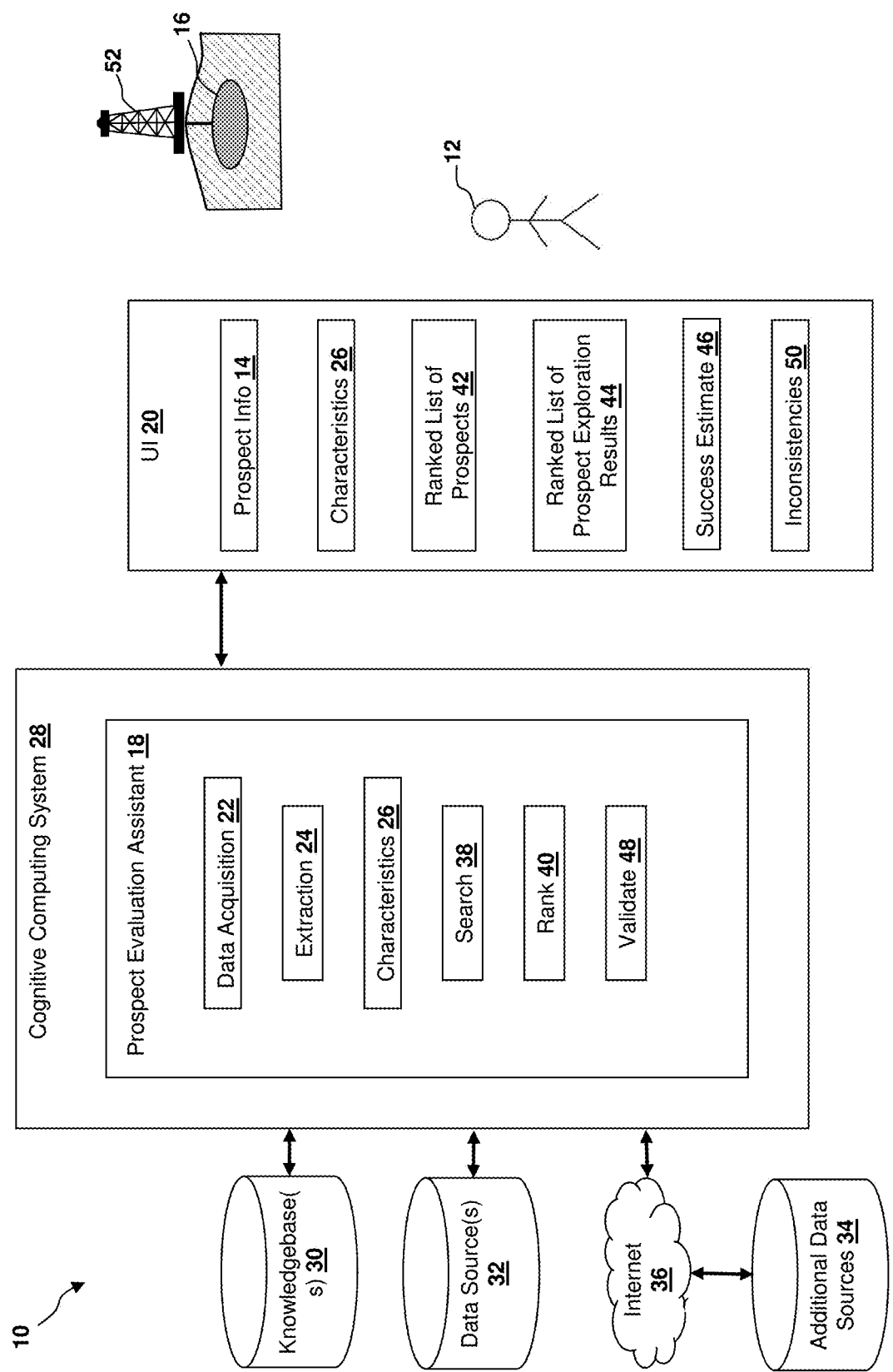
FIG. 1 depicts a system for assisting the evaluation of prospects in oil and gas exploration according to embodiments.

The drawings are not necessarily to scale. The drawings are merely schematic representations, not intended to portray specific parameters of the invention. The drawings are intended to depict only typical embodiments of the invention, and therefore should not be considered as limiting the scope of the invention. In the drawings, like numbering represents like elements.

DETAILED DESCRIPTION

Figure 2:
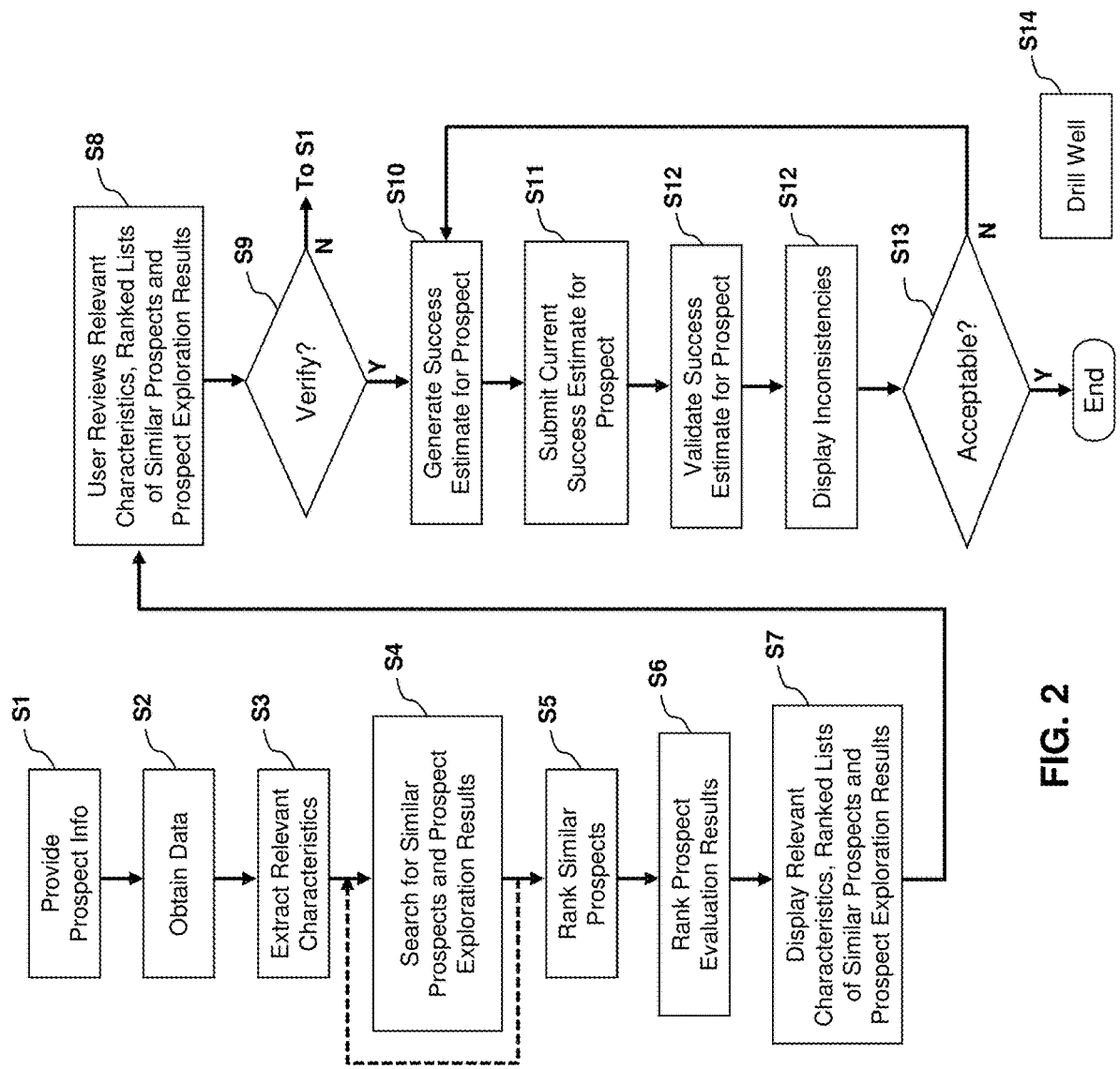
FIG. 2 depicts a flow diagram of a process carried out by the system for assisting the evaluation of prospects in oil and gas exploration of FIG. 1 according to embodiments.

Referring now to the drawings, FIG. 1 depicts a system 10 for assisting the evaluation of prospects in oil and gas exploration according to embodiments, and FIG. 2 depicts a flow diagram of a process carried out by the system for assisting the evaluation of prospects in oil and gas exploration of FIG. 1.

With reference to both to FIGS. 1 and 2, at S1, a user 12 (e.g., a geologist) provides information 14 regarding a prospect 16 to a prospect evaluation assistant 18 via a user interface 20. The prospect information 14 may include, for example, a textual description of the prospect 16, files (or links to files) containing data associated with the prospect 16, links to data sources, documents, or webpages (e.g., via a company Intranet or the Internet) associated with the prospect 16, and/or the like. The user 12 may provide a textual description of the prospect 16, for example, by answering a set of questions, which may be predefined, or by filling out fields in a questionnaire. In addition, the user 12 may reference/attach documents such as, for example, emails, reports, research notes, papers, maps, and test/survey results (e.g., gravity, seismic, magnetic) associated with the prospect 16, images (e.g., geophysical, satellite, aerial) associated with the prospect 16, and other information the user 12 feels may be pertinent to the prospect 16.

The prospect information 14 may include geophysical and geological (actual and/or modeled) data for the prospect 16. For example, the prospect information 14 may include the location of the prospect 16, the type of hydrocarbon (e.g., oil, gas, oil/gas mixture, etc.) that is expected at the prospect 16, the geological age, lithology, and depositional environment of the prospect 16, the diagnetic and structural history of the prospect 16, the porosity, hydrocarbon saturation, and permeability of the prospect 16, etc. The prospect information 14 listed above is not intended to be limiting; many other types of data associated with a prospect 16 may be provided by the user 12. The prospect information 14 may be structured (e.g., organized in some manner and easily searchable) or unstructured (e.g., does not have a pre-defined data model or is not organized in a pre-defined manner).

As described herein, a prospect 16 is associated with a potential supply of hydrocarbons in the field of oil and gas exploration. However, it should be noted that the methodology disclosed herein may be used to evaluate the exploratory risk associated with a prospect for any type of natural resource.

As S2, a data acquisition engine 22 of the prospect evaluation assistant 18 analyzes the prospect information 14 and obtains, if necessary, any data (e.g., files, images, data sources, documents) referenced in the prospect information 14. At S3, an extraction engine 24 of the prospect evaluation assistant 18 analyzes the textual description of the prospect 16 and any files, data sources, and documents provided by the user 12 in S1 and obtained by the data acquisition engine 22 in S2, and extracts an initial set of relevant characteristics 26 for the prospect 16. Such relevant characteristics 26 may include, for example, lithology, area of closure, effective porosity, water saturation and reservoir depth.

The prospect evaluation assistant 18 may be implemented using a computing system, such as a cognitive computing system 28, configured to provide data retrieval and analysis, natural language processing, machine learning, pattern recognition, predictive analysis, and data visualization. According to embodiments, machine learning algorithms and natural language processing may be used by the extraction engine 24 to analyze the prospect information 14 and extract the set of relevant characteristics 26 for the prospect 16. Different extraction algorithms may be employed to determine the set of relevant characteristics 26, depending on the nature of the prospect information 14 (e.g., structured vs. unstructured data). The cognitive computing system 28 may be coupled directly or via any suitable network to at least one knowledgebase 30 and/or at least one data source 32. Additional (e.g., external) data sources 34 may be accessed, for example, via the Internet 36.

At S4, a search engine 38 of the prospect evaluation assistant 18 performs a search for similar prospects based on the set of relevant characteristics 26 determined in S3 by the extraction engine 24. The similar prospects may include, for example, current and past prospects of the company exploring the prospect 16, prospects of competing companies, and other prospects for which data is available. The search may be performed on one or more of the knowledgebase(s) 30, data source(s) 32, and additional data sources 34. In addition, at S4, the search engine 38 searches (e.g., via the Internet) for exploration results of similar prospects based on the extracted set of relevant characteristics 26. Such exploration results may be provided, for example, via news reports/feeds, announcements, advertisements, blogs, message boards, social media, etc., that may be relevant to the prospect 16, The searches at S4 may be performed by the search engine 38 of the prospect evaluation assistant 18 as needed, or may be repeated on a periodic or continual basis to provide up to date search results (as indicated by the dashed arrow in FIG. 2). All of the data, including the prospect information 14 provided by the user 12 and the search results regarding the prospect 16, similar prospects, and the exploration results of prospects, is retained (e.g., in the knowledgebase(s) 30), and is tracked and integrated with previously stored data in a continuous learning process to facilitate and improve the evaluation (e.g., risk evaluation) of prospects.

At S5, a ranking engine 40 of the prospect evaluation assistant 18 compares the similar prospects found at S4 to the set of relevant characteristics 26 extracted at S3 for the prospect 16 and ranks the similar prospects based on the comparison. In addition, at S6, the ranking engine 40 compares the prospect exploration results found at S4 to set of relevant characteristics 26 and ranks the prospect exploration results based on the comparison. The set of relevant characteristics 26 for the prospect 16, a ranked list 42 of the similar prospects, and a ranked list 44 of the prospect exploration results are displayed to the user 12 via the user interface 20 at S7.

At S8, the user 12 reviews the set of relevant characteristics 26 for the prospect 16, the ranked list 42 of the similar prospects, and the ranked list 44 of the prospect exploration results. If the user 12 is satisfied with the set of relevant characteristics 26 for the prospect 16, the ranked list 42 of the similar prospects, and the ranked list 44 of the prospect exploration results (YES at S9), the user 12 verifies the data and flow passes to S10. If the user 12 is not satisfied (NO at S9), flow passes back to S1, where the user 12 may edit the information 14 regarding a prospect 16. S1-S9 are repeated as necessary until the user 12 is satisfied with and verifies the set of relevant characteristics 26 for the prospect 16, the ranked list 42 of the similar prospects, and the ranked list 44 of the prospect exploration results.

At S10, the user 12 generates a success estimate 46 for the prospect 16, based on the set of relevant characteristics 26 for the prospect 16, the ranked list 42 of the similar prospects, the ranked list 44 of the prospect exploration results, the expertise of the user 12, and other possible factors. The success estimate 46 may include, for example, the probability that the prospect 16 will contain hydrocarbons, the potential volume of the hydrocarbons, and the type/mixture of hydrocarbons. At S11, the user 12 inputs the success estimate 46 to the prospect evaluation assistant 18 via the user interface 18.

At S12, a validation engine 48 of the prospect evaluation assistant 18 validates the reliability of the success estimate 46 provided by the user 12 for the prospect 16. According to embodiments, the validation engine 48 may compare the success estimate 46 to the set of characteristics 26, the similar prospects, and the prospect exploration results obtained by the search engine 38 at S4, and display a list of inconsistencies 50 (if any) in the success estimate 46 via the user interface 18. This provides a double-check of the success estimate 46 provided by the user 12.

When the searches at S4 are periodically or continuously repeated by the search engine 38, the validation engine 48 is provided with up to date (e.g., current) search results for use in the validation process at S12. Further, the ranking engine 40 may update the ranked list of prospects 42 and the ranked list of prospect exploration results 44 provided to the user 12 based on the updated search results provided at S4.

At S13, based on the list of inconsistencies 50 provided by the validation engine 48, the user 12 may decide to accept and store the success estimate 46 generated in S10 (YES, S13). The process then ends. If the exploration risk for the prospect 16 is acceptable, taking the success estimate 46 and other factors into consideration, a well 52 may be drilled on the prospect at S14. Otherwise, the prospect 16 may be abandoned due to unacceptable risk.

If the user 12 decides that the success estimate 46 needs to be adjusted (NO, S13), flow returns to S10, where the user 12 may edit the success estimate 46 to address the inconsistencies 50 provided by the validation engine 48. S10-S12 are repeated as necessary until the user 12 decides that the success estimate 46 is acceptable (YES, S13).

Various aspects of the disclosure may be provided as a system, method, and/or computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out various aspects of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the disclosure are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While it is understood that the program product of the present invention may be manually loaded directly in a computer system via a storage medium such as a CD, DVD, etc., the program product may also be automatically or semi-automatically deployed into a computer system by sending the program product to a central server or a group of central servers. The program product may then be downloaded into client computers that will execute the program product. Alternatively the program product may be sent directly to a client system via e-mail. The program product may then either be detached to a directory or loaded into a directory by a button on the e-mail that executes a program that detaches the program product into a directory. Another alternative is to send the program product directly to a directory on a client computer hard drive.

Figure 3:
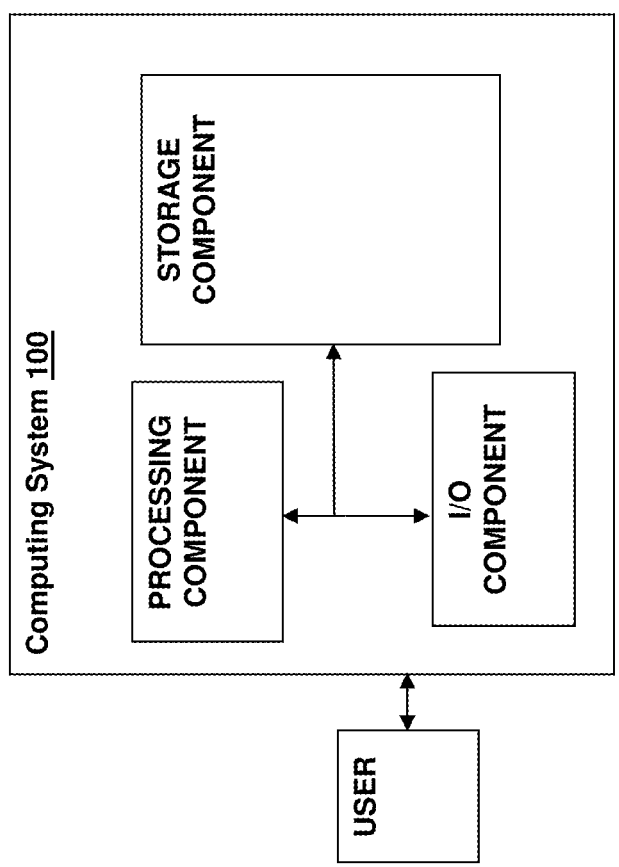
FIG. 3 depicts a computing system according to embodiments.

FIG. 3 depicts an illustrative processing system 100 for implementing various aspects of the present disclosure, according to embodiments. The processing system 100 may comprise any type of computing device and, and for example includes at least one processor, memory, an input/output (I/O) (e.g., one or more I/O interfaces and/or devices), and a communications pathway. In general, processor(s) execute program code, which is at least partially fixed in memory. While executing program code, processor(s) can process data, which can result in reading and/or writing transformed data from/to memory and/or I/O for further processing. The pathway provides a communications link between each of the components in processing system 100. I/O can comprise one or more human I/O devices, which enable a user to interact with processing system 100.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual skilled in the art are included within the scope of the invention as defined by the accompanying claims.

What is claimed is:

1. A method for evaluating a prospect, comprising:
   receiving prospect information regarding a prospect for natural resource exploration;
   extracting a set of characteristics based on the prospect information;
   identifying a set of similar prospects and a set of prospect exploration results, based on the set of characteristics;
   receiving a success estimate for the prospect;
   validating the success estimate based on the set of characteristics, the set of similar prospects, and the set of prospect exploration results to determine inconsistencies in the success estimate; and
   approving the success estimate or receiving an updated success estimate, based on the inconsistencies in the success estimate.

2. The method for evaluating a prospect according to claim 1, further comprising automatically updating the set of similar prospects and the set of prospect exploration results to provide an updated set of similar prospects and an updated set of prospect exploration results.

3. The method for evaluating a prospect according to claim 2, further comprising ranking the set of similar prospects and the set of prospect exploration results, based on a similarity to the prospect.

4. The method for evaluating a prospect according to claim 3, further comprising displaying, on a user interface, the set of characteristics, a ranked list of the similar prospects, a ranked list of the prospect exploration results, and the inconsistencies in the success estimate.

5. The method for evaluating a prospect according to claim 4, further comprising continuously updating the set of similar prospects and the set of prospect exploration results.

6. The method for evaluating a prospect according to claim 4, further comprising revalidating the success estimate to provide updated inconsistencies based on the updated set of similar prospects and the updated set of prospect exploration results.

7. The method for evaluating a prospect according to claim 6, further comprising approving the success estimate or receiving an updated success estimate, based on the updated inconsistencies.

8. The method for evaluating a prospect according to claim 1, wherein the prospect information comprises structured and unstructured data.

9. The method for evaluating a prospect according to claim 1, further comprising:
   determining if the set of characteristics, the set of similar prospects, and the set of prospect exploration results are acceptable;
   if acceptable, verifying the set of characteristics, the set of similar prospects, and the set of prospect exploration results, and providing the success estimate;
   if unacceptable, updating the set of characteristics, the set of similar prospects, and the set of prospect exploration results, and repeating the determining.

10. A computer program product stored on a computer readable storage medium, which when executed by a computing system, evaluates a prospect, the program product including program code for:
    receiving prospect information regarding a prospect for natural resource exploration;
    extracting a set of characteristics based on the prospect information;
    identifying a set of similar prospects and a set of prospect exploration results, based on the set of characteristics;
    receiving a success estimate for the prospect;
    validating the success estimate based on the set of characteristics, the set of similar prospects, and the set of prospect exploration results to determine inconsistencies in the success estimate; and
    approving the success estimate or receiving an updated success estimate, based on the inconsistencies in the success estimate.

11. The computer program product of claim 10, further including program code for automatically updating the set of similar prospects and the set of prospect exploration results to provide an updated set of similar prospects and an updated set of prospect exploration results.

12. The computer program product of claim 11, further including program code for ranking the set of similar prospects and the set of prospect exploration results, based on a similarity to the prospect.

13. The computer program product of claim 12, further including program code for displaying, on a user interface, the set of characteristics, a ranked list of the similar prospects, a ranked list of the prospect exploration results, and the inconsistencies in the success estimate.

14. The computer program product of claim 13, further including program code for continuously updating the set of similar prospects and the set of prospect exploration results.

15. The computer program product of claim 13, further comprising program code for:
    revalidating the success estimate to provide updated inconsistencies based on the updated set of similar prospects and the updated set of prospect exploration results; and approving the success estimate or receiving an updated success estimate, based on the updated inconsistencies.

16. The computer program product of claim 10, wherein the prospect information comprises structured and unstructured data.

17. The computer program product of claim 10, further comprising program code for:
  determining if the set of characteristics, the set of similar prospects, and the set of prospect exploration results are acceptable;
  if acceptable, verifying the set of characteristics, the set of similar prospects, and the set of prospect exploration results, and providing the success estimate;
  if unacceptable, updating the set of characteristics, the set of similar prospects, and the set of prospect exploration results, and repeating the determining.

18. A system for evaluating a prospect, the system comprising a prospect evaluation assistant configured for:
  receiving prospect information regarding a prospect for natural resource exploration;
  extracting a set of characteristics based on the prospect information; identifying a set of similar prospects and a set of prospect exploration
  results, based on the set of characteristics;
  receiving a success estimate for the prospect;
  validating the success estimate based on the set of characteristics, the set of similar prospects, and the set of prospect exploration results to determine inconsistencies in the success estimate; and
  approving the success estimate or receiving an updated success estimate, based on the inconsistencies in the success estimate.

19. The system for evaluating a prospect according to claim 18, further comprising:
  automatically updating the set of similar prospects and the set of prospect exploration results to provide an updated set of similar prospects and an updated set of prospect exploration results;
  revalidating the success estimate to provide updated inconsistencies based on the updated set of similar prospects and the updated set of prospect exploration results; and
  approving the success estimate or receiving an updated success estimate, based on the updated inconsistencies.

20. The system for evaluating a prospect according to claim 18, further comprising:
  determining if the set of characteristics, the set of similar prospects, and the set of prospect exploration results are acceptable;
  if acceptable, verifying the set of characteristics, the set of similar prospects, and the set of prospect exploration results, and providing the success estimate;
  if unacceptable, updating the set of characteristics, the set of similar prospects, and the set of prospect exploration results, and repeating the determining.

* * * * *